US009045576B2

(12) United States Patent
Jiang et al.

(10) Patent No.: US 9,045,576 B2
(45) Date of Patent: *Jun. 2, 2015

(54) MIXED CHARGE COPOLYMERS AND HYDROGELS

(75) Inventors: Shaoyi Jiang, Redmond, WA (US);
Shengfu Chen, Zhejiang (CN)

(73) Assignee: University of Washington, Seattle, WA (US)

( * ) Notice: Subject to any disclaimer, the term of this patent is extended or adjusted under 35 U.S.C. 154(b) by 1018 days.

This patent is subject to a terminal disclaimer.

(21) Appl. No.: 12/367,744

(22) Filed: Feb. 9, 2009

(65) Prior Publication Data

US 2009/0259015 A1 Oct. 15, 2009

Related U.S. Application Data

(63) Continuation of application No. PCT/US2007/075409, filed on Aug. 7, 2007.

(60) Provisional application No. 60/821,685, filed on Aug. 7, 2006.

(51) Int. Cl.
| | | |
|---|---|---|
| *B32B 19/00* | (2006.01) | |
| *C08F 220/26* | (2006.01) | |
| *C08F 220/34* | (2006.01) | |
| *B29C 39/20* | (2006.01) | |
| *C08L 51/04* | (2006.01) | |
| *C08F 222/10* | (2006.01) | |

(52) U.S. Cl.
CPC ............ *C08F 220/26* (2013.01); *B29C 39/20* (2013.01); *C08L 51/04* (2013.01); *C08F 220/34* (2013.01); *C08F 222/1006* (2013.01)

(58) Field of Classification Search
CPC ................................ C08L 51/04; B29C 39/20
USPC ................... 514/100; 528/332; 428/357, 458
See application file for complete search history.

(56) References Cited

U.S. PATENT DOCUMENTS

| | | | |
|---|---|---|---|
| 3,671,502 A | 6/1972 | Samour | |
| 4,138,446 A | 2/1979 | Kawakami | |
| 5,204,060 A | 4/1993 | Allenmark | |
| 6,361,768 B1 * | 3/2002 | Galleguillos et al. | 424/70.12 |
| 6,486,333 B1 | 11/2002 | Murayama | |
| 6,897,263 B2 | 5/2005 | Hell | |
| 7,306,625 B1 | 12/2007 | Stratford | |
| 7,335,248 B2 | 2/2008 | Abou-Nemeh | |
| 7,737,224 B2 | 6/2010 | Willis | |
| 2002/0128234 A1 * | 9/2002 | Hubbell et al. | 514/100 |
| 2005/0058689 A1 | 3/2005 | McDaniel | |
| 2007/0169814 A1 * | 7/2007 | Huck et al. | 136/263 |

FOREIGN PATENT DOCUMENTS

| | | |
|---|---|---|
| DE | 10 2006 004 111 A1 | 8/2007 |
| EP | 0 354 984 A2 | 2/1990 |
| EP | 0 419 654 A1 | 4/1991 |
| EP | 0 479 245 A2 | 4/1992 |
| JP | 63-234007 A | 9/1988 |
| JP | 2007-130194 A | 5/2007 |
| SU | 1780673 A1 | 12/1992 |
| WO | 00/39176 A1 | 7/2000 |
| WO | 2004/058837 A2 | 7/2004 |
| WO | 2005/100666 A1 | 11/2004 |

OTHER PUBLICATIONS

Zhao Multivariate statistical analysis of protein variation, PhD thesis, UNC, Sep. 2005.*
Chang, Y., et al., "Highly Protein-Resistant Coatings From Well-Defined Diblock Copolymers Containing Sulfobetaines," Langmuir 22(5):2222-2226, Feb. 2006.
Chen, S., et al., "Controlling Antibody Orientation on Charged Self-Assembled Monolayers," Langmuir 19(7):2859-2864, Apr. 2003.
Chen, S., et al., "Strong Resistance of Oligo(phosphorylcholine) Self-Assembled Monolayers to Protein Adsorption," Langmuir 22(6):2418-2421, Mar. 2006.
Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.
Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.
Feng., W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12):2931-2942, Jun. 2004.
Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.
Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.
Li, L., et al., "Protein Adsorption on Alkanethiolate Self-Assembled Monolayers: Nanoscale Surface Structural and Chemical Effects," Langmuir 19(7):2974-2982, Apr. 2003.
Li, L.. et al "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.
Lowe, A.B., et al., "Well-Defined Sulfobetaine-Based Statistical Copolymers as Potential Antibioadherent Coatings," Journal of Biomedical Materials Research 52(1):88-94, Jul. 2000.
West, S.L., et al., "The Biocompatibility of Crosslinkable Copolymer Coatings Containing Sulfobetaines and Phosphobetaines," Biomaterials 25:1195-1204, Apr. 2004.

(Continued)

*Primary Examiner* — Gregory Listvoyb

(74) *Attorney, Agent, or Firm* — Christensen O'Connor Johnson Kindness PLLC

(57) ABSTRACT

Nonfouling copolymers and hydrogels comprising positively charged repeating units or latent positively charged repeating units and negatively charged units or latent positively charged units.

11 Claims, 10 Drawing Sheets

(56) References Cited

OTHER PUBLICATIONS

Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.

Yuan, J., et al., "Improvement of Blood Compatibility on Cellulose Membrane Surface by Grafting Betaines," Colloids and Surfaces B: Biointerfaces 30(1-2):147-155, Jul. 2003.

Yuan, J., "Platelet Adhesion Onto Segmented Polyurethane Surfaces Modified by Carboxybetaine," Journal of Biomaterial Science, Polymer Edition 14(12):1339-1349, Dec. 2003.

Yuan, Y., et al., "Grafting Sulfobetaine Monomer Onto Silicone Surface to Improve Haemocompatability," Polymer International 53(1):121-126, Jan. 2004.

Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.

Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.

Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.

Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.

Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.

Zhang, Z., et al., "Superflow Fouling Sulfobetaine and Carboxybetaine Polymers on Glass Slides," Langmuir 22(24):10072-10077, Nov. 2006.

Zhang, Z., "Surface Grafted Sulfobetaine Polymers Via Atom Transfer Radical Polymerization as Superlow Fouling Coatings," Journal of Physical Chemistry B 110(22):10799-10804, Jun. 2006.

Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.

Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.

Zhou, J., et al., "Platelet Adhesion and Protein Adsorption on Silicone Rubber Surface by Ozone-Induced Grafted Polymerization With Carboxybetaine Monomer," Colloids and Surfaces B: Biointerfaces 41(1):55-62, Mar. 2005.

\* cited by examiner

MIXED CHARGE COPOLYMERS AND HYDROGELS

CROSS-REFERENCE TO RELATED APPLICATIONS

This application is a continuation of PCT/US2007/075409, filed Aug. 7, 2007, which claims the benefit of U.S. Provisional Application No. 60/821,685 filed Aug. 7, 2006. Each application is incorporated herein by reference in its entirety.

STATEMENT OF GOVERNMENT LICENSE RIGHTS

This invention was made with government support under Contract No. N000140410409, awarded by the Office of Naval Research and Contract No. CTS0433753 awarded by the National Science Foundation. The Government has certain rights in the invention.

BACKGROUND OF THE INVENTION

A major challenge in the field of biomaterials is the prevention of nonspecific protein adsorption on surfaces. Nonspecific protein adsorption on surfaces has varieties of adverse affects. For example, nonspecific protein adsorption degrades the performance of surface-based diagnostic devices and slows the healing process for implanted biomaterials.

Nonfouling or low fouling materials can be used to address nonspecific protein adsorption on surfaces. For example, pegylated background has been applied to biosensor platforms to prevent nonspecific adsorption from complex media. Nonfouling materials can also be used for marine coatings to replace the existing toxic tributyltin (TBT) coatings to prevent biofouling on ships.

There are limited number of effective nonfouling materials that can meet various challenges for practical applications. Two nonfouling materials, polyethylene glycol (PEG) and phosphorylcholine (PC)-based materials, have been extensively studied. However, there are shortcomings with these materials, such as that PEG is subject to oxidation and that 2-methacryloyloxylethyl phosphoryleholine (MPC) monomers are not readily available. In addition, both PEG and PC groups lack functional groups available for ligand immobilization as required for many applications. The introduction of additional functional groups into PEG may alter its nonfouling properties.

Therefore, there is a need for nonfouling materials that circumvents limitations of oxidation and can be formed from varieties of readily available compounds. The present invention seeks to fulfill these needs and provides further related advantages.

SUMMARY OF THE INVENTION

The present invention provides nonfouling copolymers and hydrogels.

In one aspect, the present provides copolymers that include, (a) a plurality of repeating units independently selected from negatively charged repeating units and repeating units having latent negatively charged groups reactive to provide negatively charged groups; and (b) a plurality of repeating units independently selected from positively charged repeating units and repeating units having latent positively charged groups reactive to provide positively charged groups.

In one embodiment, the copolymer is crosslinked to provide a hydrogel. In one embodiment, the copolymer can further include a plurality of repeating units having a hydrophobic pendant group. In one embodiment, the copolymer is synthesized on a surface via atom transfer radical polymerization.

In one embodiment, the copolymer and hydrogel of the present invention have at least a portion of the charged repeating units comprise a repeating unit having a charged pendant group. In one embodiment, the copolymer and hydrogel of the present invention have at least a portion of the charged repeating units comprise a repeating unit having a charged monomeric backbone group. In one embodiment, the backbone of the copolymers and hydrogels of the present invention comprise both negative charges and positive charges.

In one embodiment, the copolymers and hydrogels of the present invention comprise a plurality of positively charged repeating units having a positively charged pendant group. Representative positively charged pendant groups include a quaternary ammonium group, a primary amine group, a secondary amine group, a tertiary amine group, a quaternary phosphonium group, a tertiary phosphonium group, an amide group, a heteroaromatic nitrogen group, and a sulfonium group. In one embodiment, the copolymers and hydrogels of the present invention comprise a plurality of negatively charged repeating units having a negatively charged pendant group. Representative negatively charged pendant groups include a sulfuric acid group, a carboxylic acid group, a phosphoric acid group, a nitric acid group, a phenol group, and a sulfonamide group.

In one embodiment, the copolymers and hydrogels of the present invention comprise the repeating units having latent negatively charged groups, wherein the latent negatively charged groups are selected from the group consisting of a sulfuric acid ester group, a carboxylic acid ester group, a phosphoric acid ester group, a sulfone group, a sulfide group, a disulfide group, an ortho ester group, an anhydride group, and a beta-ketosulfone group. In one embodiment, the copolymers and hydrogels of the present invention comprise the repeating units having latent positively charged groups, wherein the latent positively charged groups are selected from the group consisting of an imide group and an oxyimino group.

The latent negatively charged groups and latent positively charged groups in the copolymers and hydrogels of the present invention can be converted to charged groups upon exposure to an oxidant, a reductant, heat, light, an acid, a base, an enzyme, or electromagnetic field.

Any monomer that is capable of polymerization can be used for the present invention. Representative monomers that are useful in the present invention include acrylate, styrene, acrylamide, vinyl compounds, epoxides and mixtures thereof. In one embodiment, at least one of the negatively charged repeating units, the repeating units having latent negatively charged groups, the positively charged repeating units, and the repeating units having latent positively charged groups is derived from amino acid-based monomer.

In one embodiment, the ratio of the number of the negatively charged repeating units or the repeating units having latent negatively charged groups to the number of the positively charged repeating units or repeating units having latent positively charged groups is from about 1:1.1 to about 1:0.5. In one embodiment, the ratio of the number of the negatively charged repeating units or the repeating units having latent negatively charged groups to the number of the positively charged repeating units or repeating units having latent positively charged groups is from about 1:1.1 to about 1:0.7. In one embodiment, the ratio of the number of the negatively charged repeating units or the repeating units having latent negatively charged groups to the number of the positively charged repeating units or repeating units having latent positively charged groups is from about 1:1.1 to about 1:0.9.

In one embodiment, the present invention provides copolymer that include a plurality of negatively charged repeating units and a plurality of positively charged repeating units.

In one embodiment, the present invention provides copolymer that include a plurality repeating of units having latent negatively charged groups reactive to provide negatively charged groups and a plurality of positively charged repeating units, wherein the copolymer is substantially electronically neutral when the latent negatively charged groups are converted to negatively charged groups.

In one embodiment, the present invention provides copolymer that include a plurality of negatively charged repeating units and a plurality of repeating units having latent positively charged groups reactive to provide positively charged groups, wherein the copolymer is substantially electronically neutral when the latent positively charged groups are converted to positively charged groups.

In one embodiment, the present invention provides copolymer that include a plurality of repeating units having latent negatively charged groups reactive to provide negatively charged groups and a plurality of repeating units having latent positively charged groups reactive to provide positively charged groups, wherein the copolymer is substantially electronically neutral when the latent negatively charged groups are converted to negatively charged groups, and the latent positively charged groups are converted to positively charged groups.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1A:
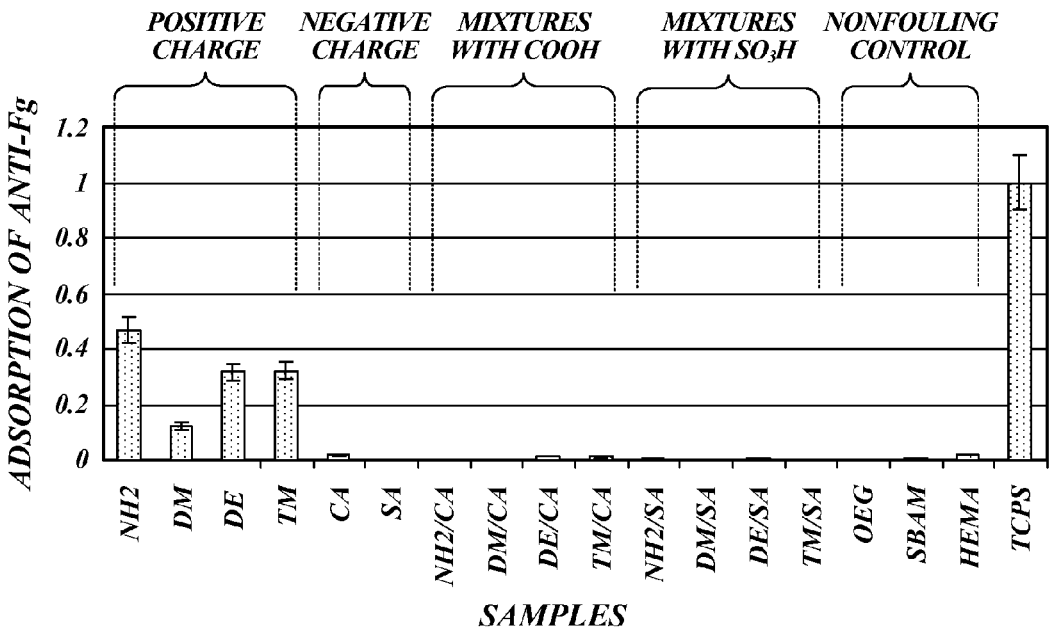
FIG. 1A compares the HRP conjugated anti-fibrinogen adsorption for various hydrogels.

The present invention provides copolymers and hydrogels including both positively charged units or latent positively charged units and negatively charged units or latent positively charged units. The copolymers and hydrogels of the present invention are low fouling or nonfouling materials with unique properties resulting from various designed functional groups.

As used herein, "polyampholytes" are polymers with both positively and negatively charged groups.

As used herein, "latent positively charged group" is a functional group that can be converted to positively charged group when exposed to an appropriate environmental stimulus.

As used herein, "latent negatively charged group" is a functional group that can be converted to negatively charged group when exposed to an appropriate environmental stimulus.

As used herein, "repeating unit" means a unit derived from a negative- or positive-charged monomer used to form the polymers or hydrogels of the invention.

ABBREVIATIONS AND NOMENCLATURES

AIBN Azobisisobutylonitrile
C12 Lauryl methacrylate
CA 2-Carboxyethyl acrylate
DE 2-(Diethylamino) ethyl methacrylate
DM 2-(Dimethylamino)ethyl methacrylate
DMF Dimethylformamide
E Glutamic Acid
EDT 1,2-ethanedithiol
ELISA Enzyme-linked Immunosorbent Assay
GL Ethyl glycolate methacrylate IB Isobutyl methacrylate
K Lysine
Me Methyl methacrylate
NH$_2$ 2-Aminoethyl methacrylate hydrochloride
PEG Poly(ethylene glycol) methacrylate
SP 3-Sulfopropyl methacrylate potassium salt
TCPS Tissue culture polystyrene
TFA Trifluoroacetic acid
TFE 2,2,2-Trifluoroethyl methacrylate
TM [2-(Methacryloyloxy)ethyl] trimethylammonium chloride The present invention provides nonfouling copolymers and hydrogels.

In one aspect, the present provides copolymers that include, (a) a plurality of repeating units independently selected from negatively charged repeating units and repeating units having latent negatively charged groups reactive to provide negatively charged groups; and (b) a plurality of repeating units independently selected from positively charged repeating units and repeating units having latent positively charged groups reactive to provide positively charged groups.

In one embodiment, the copolymer is crosslinked to provide a hydrogel. In one embodiment, the copolymer can further include a plurality of repeating units having a hydrophobic pendant group. In one embodiment, the copolymer is synthesized on a surface via atom transfer radical polymerization.

In one embodiment, the copolymer and hydrogel of the present invention have at least a portion of the charged repeating units comprise a repeating unit having a charged pendant group. In one embodiment, the copolymer and hydrogel of the present invention have at least a portion of the charged repeating units comprise a repeating unit having a charged monomeric backbone group. In one embodiment, the backbone of the copolymers and hydrogels of the present invention comprise both negative charges and positive charges.

In one embodiment, the copolymers and hydrogels of the present invention comprise a plurality of positively charged repeating units having a positively charged pendant group. In one embodiment, the copolymers and hydrogels of the present invention comprise a plurality of negatively charged repeating units having a negatively charged pendant group.

In one embodiment, the copolymers and hydrogels of the present invention comprise the repeating units having latent negatively charged groups, wherein the latent negatively charged groups are selected from the group consisting of a sulfuric acid ester group, a carboxylic acid ester group, a phosphoric acid ester group, a sulfone group, a sulfide group, a disulfide group, an ortho ester group, an anhydride group, and a beta-ketosulfone group. In one embodiment, the copolymers and hydrogels of the present invention comprise the repeating units having latent positively charged groups, wherein the latent positively charged groups are selected from the group consisting of an imide group and an oxyimino group.

The latent negatively charged groups and latent positively charged groups in the copolymers and hydrogels of the present invention can be converted to charged groups upon exposure to an oxidant, a reductant, heat, light, an acid, a base, an enzyme, or electromagnetic field.

Any monomer that is capable of polymerization can be used for the present invention. Representative monomers that are useful in the present invention include acrylate, styrene, acrylamide, vinyl compounds, epoxides and mixtures thereof. In one embodiment, at least one of the negatively charged repeating units, the repeating units having latent negatively charged groups, the positively charged repeating units, and the repeating units having latent positively charged groups is derived from amino acid-based monomer.

In one embodiment, the ratio of the number of the negatively charged repeating units or the repeating units having latent negatively charged groups to the number of the positively charged repeating units or repeating units having latent positively charged groups is from about 1:1.1 to about 1:0.5. In one embodiment, the ratio of the number of the negatively charged repeating units or the repeating units having latent negatively charged groups to the number of the positively charged repeating units or repeating units having latent positively charged groups is from about 1:1.1 to about 1:0.7. In one embodiment, the ratio of the number of the negatively charged repeating units or the repeating units having latent negatively charged groups to the number of the positively charged repeating units or repeating units having latent positively charged groups is from about 1:1.1 to about 1:0.9.

Copolymers and Hydrogels with Negatively and Positively Charged Groups

In one embodiment, the present invention provides a copolymer, comprising, (a) a plurality of negatively charged repeating units; and (b) a plurality of positively charged repeating units, wherein the copolymer is substantially electronically neutral.

As used herein, the term "substantially electronically neutral" means that the number of positively charged repeating units and the number of the negatively charged repeating units are substantially equal, and that there is a uniform distribution of mixed charged groups at the nanometer scale.

In the copolymers and hydrogels of the present invention, one charge is surrounded by its opposite charge, and the solvation or electric double layers between two opposite charges are in contact.

In one embodiment, the copolymer is crosslinked to provide a hydrogel.

The copolymers and hydrogels of the present invention are not block copolymers. In the copolymers and hydrogels of the present invention, there is no stretch of more than 10 consecutive units with the same charge in these polymers, and the negatively charged repeating units and the positively charged repeating units are substantially balanced. In one embodiment, the ratio of the number of the negatively charged repeating units to the number of the positively charged repeating units is from about 1:1.1 to about 1:0.5. In one embodiment, the ration of the number of negatively charged repeating units to the number of positively charged repeating units is from about 1:1.1 to about 1:0.7. In one embodiment, the ration of the number of negatively charged repeating units to the number of positively charged repeating units is from about 1:1.1 to about 1:0.9. In one embodiment, the copolymers and hydrogels have an alternating charge distribution, i.e., each negative charged unit is connected to a positively charged unit.

The negatively charged repeating unit maybe a repeating unit having a negatively charged pendant group or a repeating unit having a negative charge in its monomeric backbone structure. The negatively charged pendant group can be any group with a negative charge. Representative negatively charged pendant groups include sulfuric acid groups, sulfonic acid groups, carboxylic acid groups, phosphoric acid groups, phosphonic acid groups, phenol groups, and sulfonamide groups.

The negatively charged repeating unit can be derived from a monomer having a negatively charged pendant group or a negatively charged backbone. Representative monomers that can be used to derive the negatively charged repeating unit copolymers and hydrogels of in the copolymers and hydrogels of the present invention include 2-carboxyethyl acrylate, 3-sulfopropyl methacrylate, lauryl methacrylate, isobutyl methacrylate, 2,2,2-trifluoroethyl methacrylate, and poly (ethylene glycol) methacrylate, and D-glucuronic acid.

The positively charged repeating unit may be a repeating unit having a positively charged pendant group or a repeating unit having a positive charge on its monomeric backbone structure. The positively charged pendant group can be any group with a positive charge. Representative positively charged pendant groups include quaternary ammonium groups, primary amine groups, secondary amine groups, tertiary amine groups, quaternary phosphonium groups, tertiary phosphonium groups, amide groups, heteroaromatic nitrogen groups, sulfonium groups, and metallic organic acids.

The positively charged repeating unit can be derived from a monomer having a positively charged pendant group or a positively charged backbone. Representative monomers that can be used to derive the positively charged repeating unit in the copolymers and hydrogels of the present invention include 2-(dimethylamino)ethyl methacrylate, 2-(diethylamino)ethyl methacrylate, [2-(methacryloyloxy)ethyl] trimethylammonium chloride, and N-acetylglucosamine.

In the present invention, the repeating units can be derived from any monomer that is capable of polymerization and forming a polymer. Representative monomers include methacrylate, acrylate, styrene, acrylamide, vinyl compounds, epoxide, and mixture thereof.

In one embodiment, the negatively charged repeating unit is derived from 3-sulfopropyl methacrylate potassium salt (SP), and the positively charged repeating unit is derived from 2-(dimethylamino)ethyl methacrylate (DM). In one embodiment, the negatively charged repeating unit is derived from 3-sulfopropyl methacrylate potassium salt (SP), and the positively charged repeating unit is derived from [2-(methacryloyloxy)ethyl]trimethylammonimium chloride (TM). In one embodiment, the negatively charged repeating unit is derived from isobutyl methacrylate (IB), and the positively charged repeating unit is derived from 2-(dimethylamino)ethyl methacrylate (DM). In one embodiment, the negatively charged repeating unit is derived from 2,2,2-trifluoroethyl methacrylate (TFE), and the positively charged repeating unit is derived from 2-(dimethylamino)ethyl methacrylate (DM).

Representative copolymers and hydrogels of the present invention were prepared from positively charged compounds including aminoethyl methacrylate hydrochloride (NH2), (2-(dimethylamino)ethyl methacrylate (DM), 2-(diethylamino) ethyl methacrylate (DE), and 2-(methacryloyloxy)ethyl trimethylammonium chloride (TM), and negatively charged compounds including 2-carboxyethyl acrylate (CA), and 3-sulfopropyl methacrylate potassium salt (SA).

In one embodiment, the hydrogel NH2/CA has the negatively charged repeating unit derived from 2-carboxyethyl acrylate (CA) and the positively charged repeating unit derived from 2-aminoethyl methacrylate hydrochloride (NH2).

In one embodiment, the hydrogel DM/CA has the negatively charged repeating unit derived from 2-carboxyethyl acrylate (CA) and the positively charged repeating unit derived from 2-(dimethylamino)ethyl methacrylate (DM).

In one embodiment, the hydrogel DE/CA has the negatively charged repeating unit derived from 2-carboxyethyl acrylate (CA) and the positively charged repeating unit derived from 2-(diethylamino)ethyl methacrylate (DE).

In one embodiment, the hydrogel TM/CA has the negatively charged repeating unit derived from 2-carboxyethyl acrylate (CA) and the positively charged repeating unit derived from [2-(methacryloyloxy)ethyl]trimethylammonimium chloride (TM).

In one embodiment, the hydrogel $NH_2$/SA has the negatively charged repeating unit derived from 11-mercaptoundecylsulfonic acid (SA) and the positively charged repeating unit derived from 2-aminoethyl methacrylate hydrochloride (NH2).

In one embodiment, the hydrogel DM/SA has the negatively charged repeating unit derived from 3-sulfopropyl methacrylate potassium salt (SA) and the positively charged repeating unit derived from 2-(dimethylamino)ethyl methacrylate (DM).

In one embodiment, the hydrogel DE/SA has the negatively charged repeating unit derived from 3-sulfopropyl methacrylate potassium salt (SA) and the positively charged repeating unit derived from 2-(diethylamino)ethyl methacrylate (DE).

In one embodiment, the hydrogel TM/SA has the negatively charged repeating unit derived from 3-sulfopropyl methacrylate potassium salt (SA) and the positively charged repeating unit derived from [2-(methacryloxy)ethyl]trimethylammonimium chloride (TM).

In preparing the representative hydrogels, the positively charged monomer and the negatively charged monomer in a mixed solvent of ethylene glycol/ethanol/$H_2O$ (1.5:1:1.5) were mixed with triethyleneglycol-dimethacrylate (TEGDMA), ammonium persulfate (APS) and sodium metabisulfite (SMS). The mixture was placed between two glass slides, placed into a 60° C. oven for one hour, and left at room temperature for 3 hours to provide a hydrogel film.

The copolymers and hydrogels of the present invention have low fouling or nonfouling properties. Not wanting to be limited by the theory, it is believed that in the copolymers and hydrogels of the invention, the positively and negatively charged pendant groups self-organize into a uniform mixed charged state at the nanometer scale, leading to a nonfouling surface.

Enzyme-linked immunosorbent assay (ELISA) experiments were used to evaluate the low fouling or nonfouling properties of the representative hydrogels. The nonfouling controls were oligo(ethylene glycol) methacrylate (OEG, typical Mn=300), sulfobetaine methylacrylate (SBMA), and 2-hydroxyethyl methacrylate (HEMA). Tissue culture polystyrene (TCPS) was used as a fouling reference.

Figure 1B:
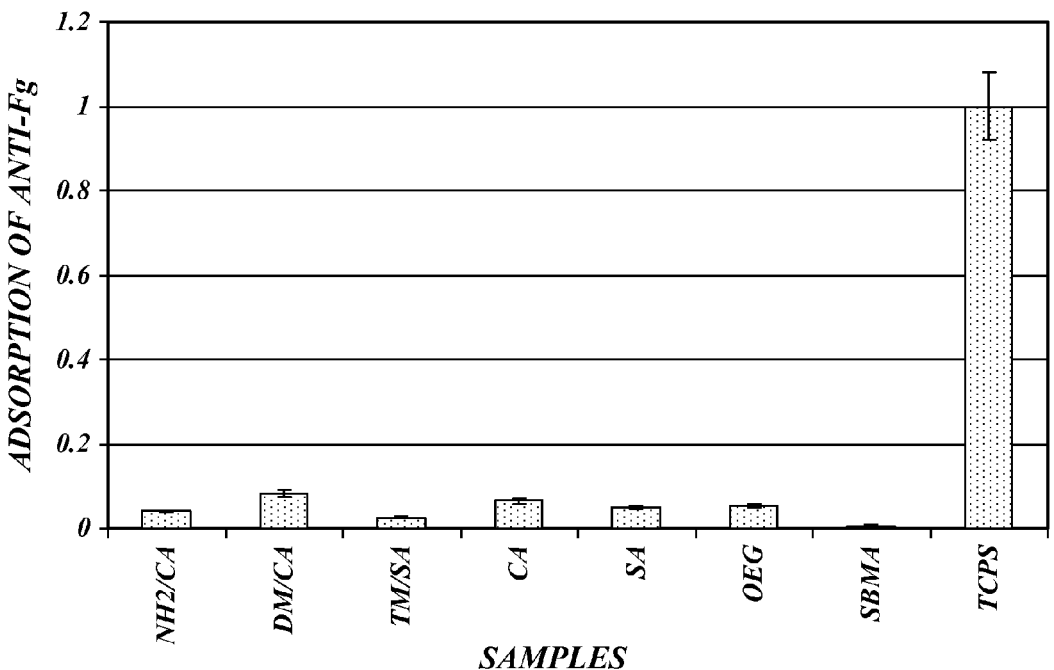
FIG. 1B compares the fibrinogen (Fg) adsorption detected by conjugated anti-Fg HRP to selected hydrogels from pH 7.4, 150 mM PBS buffer.

It is shown from ELISA experiments that IgG adsorption on hydrogels prepared from mixed charged compounds is very low under physiological conditions (FIG. 1A). However, significant IgG adsorption was observed on all of the hydrogels containing positively charged compounds. While protein adsorption on these surfaces was performed mainly with IgG, fibrinogen (Fg) adsorption on selected surfaces was also tested. Fg is a model protein commonly used to evaluate surfaces for their nonspecific protein adsorption because Fg usually adsorbs more easily than other proteins. Results for Fg adsorption show a similar trend as those for IgG adsorption under physiological conditions (FIG. 1B). These results indicate that nonfouling hydrogels can be readily prepared from a variety of functional groups.

Figure 2A:
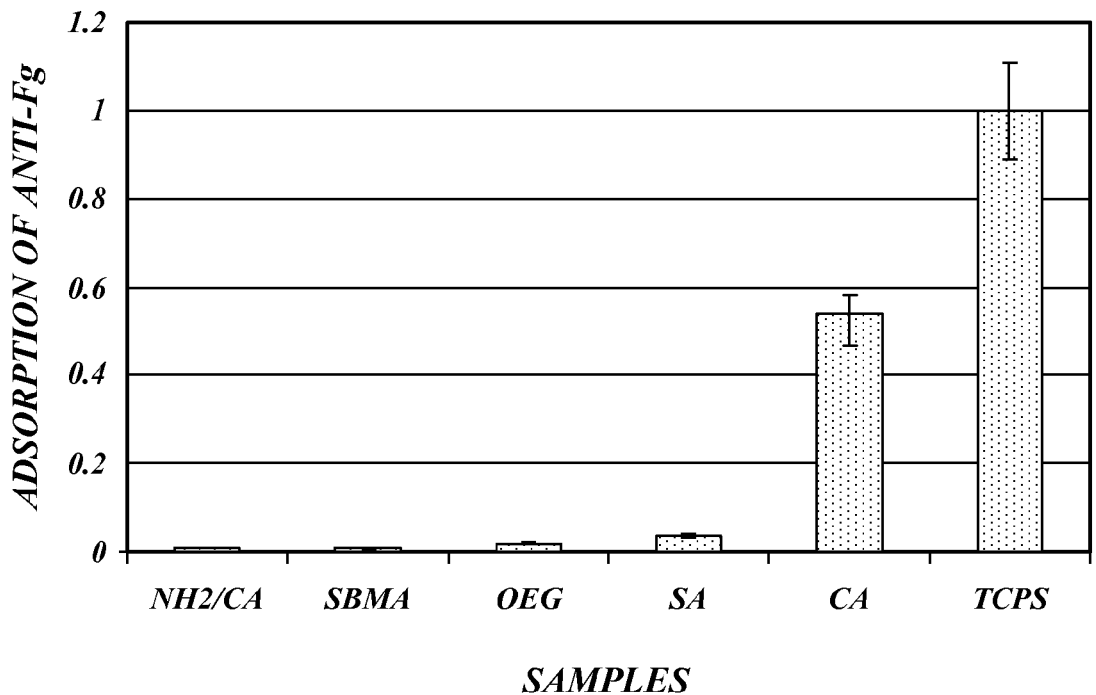
FIG. 2A compares HRP conjugated anti-fibrinogen adsorption to hydrogels from 2 mM, pH 7.4 PBS.
Figure 2B:
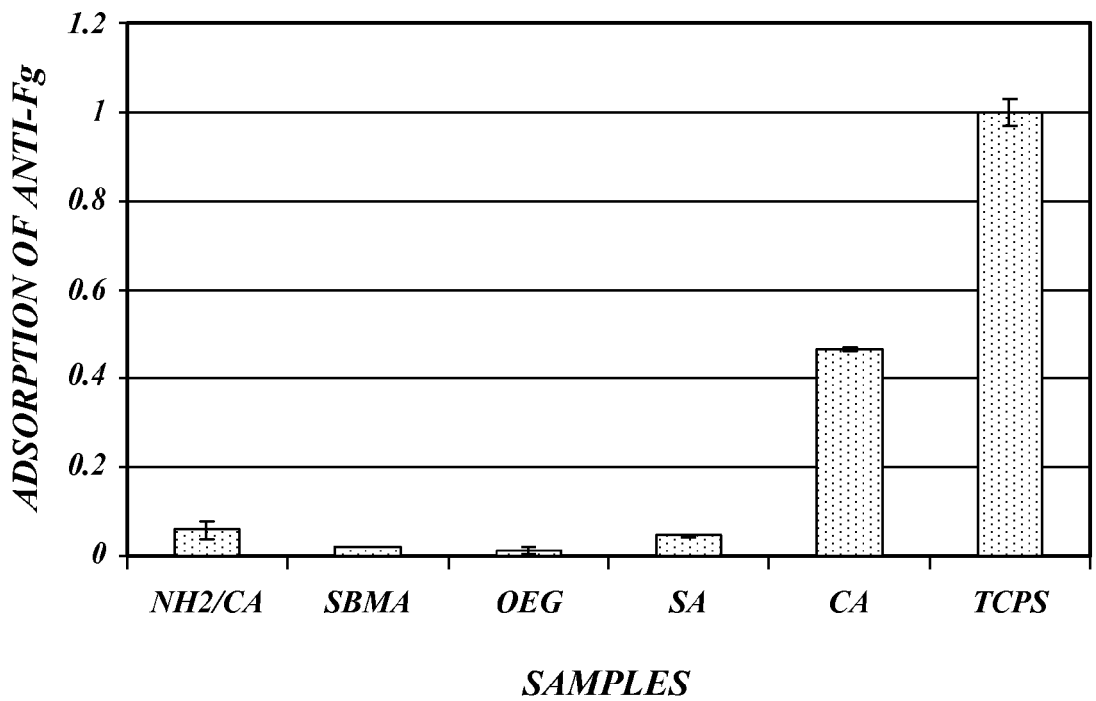
FIG. 2B compares HRP conjugated anti-fibrinogen adsorption to hydrogels from 10 mM, pH 5 PBS.

Similar to OEG and SBMA, protein adsorption on the charge-balanced polyampholyte $NH_2$/CA hydrogel is less than 5% (FIGS. 2A and 2B) even when pH and ionic strengths are away from physiological conditions. Protein adsorption on these surfaces is shown to not be very sensitive to changes in pH or ionic strength. This indicates that there is a close similarity in protein adsorption between zwitterionic polymers (i.e., positive and negative charges in the same side chain such as SBMA) and mixed charged polymers (i.e., positive and negative charges in different side chains such as $NH_2$/CA hydrogel). It is expected that $NH_2$ and CA components in the $NH_2$/CA hydrogel promote the protonation and deprotonation of each other, respectively, under both pH values of 5 and 7.4 because they are geometrically close enough. Thus, mixed $NH_2$/CA hydrogel maintains its nonfouling behavior as zwitterionic SBMA. These results indicate that charge balanced polyampholytes exhibit strong resistance to nonspecific protein adsorption.

The positive charge and negative charge can be on the backbone of the copolymers and hydrogels of the present invention. Preferably, the backbone of the copolymers and hydrogels have alternating positive charge and negative charge. For example, the polymers formed from poly(ortho esters) and tertiary amine or other low active organic bases can have alternating positive and negative charges on the backbone of the polymers.

Copolymers and Hydrogels with Latent Negatively Charged Groups and Positively Charged Groups In one embodiment, the present invention provides a copolymer, comprising, (a) a plurality of repeating units having latent negatively charged groups reactive to provide negatively charged groups; and (b) a plurality of positively charged repeating units, wherein the copolymer is substantially electronically neutral when the latent negatively charged groups are converted to negatively charged groups.

The copolymer can be crosslinked to provide a hydrogel.

The latent negatively charged group is a group that can be converted to a negatively charged group upon exposure to an appropriate environmental stimulus. Representative environmental stimuli include oxidants, reductant, heat, light, acid, base, enzyme, and electromagnetic field. The latent negatively charged group can be an ester, an ortho ester, or an anhydride. Representative latent negatively charged group includes sulfuric acid ester groups, carboxylic acid ester groups, phosphoric acid ester groups, nitric acid ester groups, ortho ester groups, anhydride groups, sulfide groups, disulfide groups, and beta-ketosulfone groups.

The repeating unit having a latent negatively charged group can be derived from a monomer having a latent negatively charged group. Representative monomers include sulfuric acid ester groups, carboxylic acid ester groups, phosphoric acid ester groups, nitric acid ester groups, sulfide groups, carbohydrate monomer groups, and amino acid groups.

Figure 8:
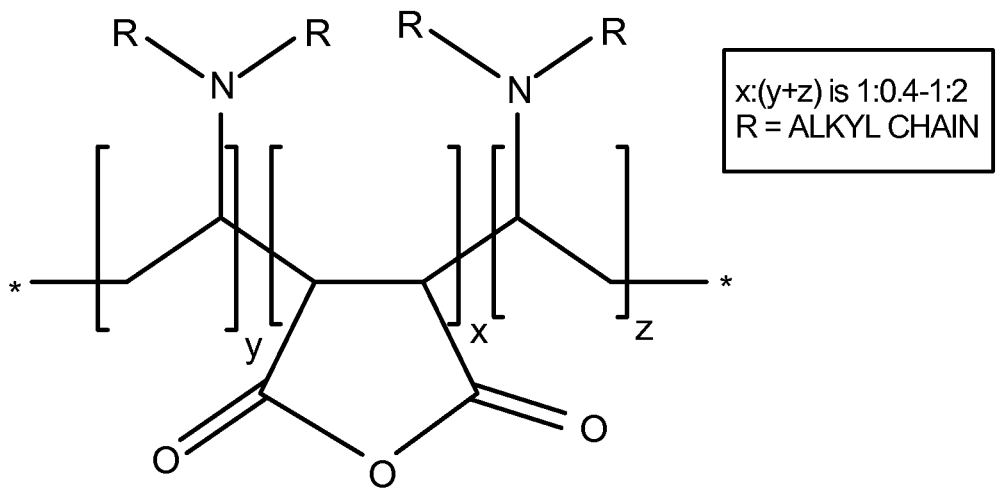
FIG. 8 is a schematic illustration of a representative copolymer with latent negatively charged groups as anhydride groups.

In one embodiment, as shown in FIG. 8, the latent negatively charged groups are anhydride groups and the positively charged groups are amines. The hydrolysis of the anhydride groups provides negatively charged carboxylic acid groups.

In one embodiment, the repeating unit having latent negatively charged group is derived from ethyl glycollate methacrylate (GL), and the positively charged repeating unit is derived from 2-(dimethyamino)ethyl methacrylate (DM).

Representative GL/DM hydrogel of the present invention was prepared from GL and DM monomers. GL and DM in a 1:1 molar ratio along with AIBN were mixed in ethyl acetate. The solution was purged by nitrogen for 30 minutes. The solution was continuously stirred and polymerized to yield a copolymer solution. Aluminum or epoxy-coated aluminum coated panels were coated using the dip-in method with the copolymer solution. Protein adsorption was evaluated by ELISA after the coated sample surface was hydrolyzed in 3.5% NaCl solution (pH 8.3) at 25° C. for different time intervals. The results in FIG. 12 demonstrate that with the hydrolysis of the latent negatively charged group, the protein adsorption on the hydrogel coated surface decreases.

In one embodiment, the repeating unit having a latent negatively charged group is derived from Isobutyl methacrylate (IB), and the positively charged repeating unit is derived from 2-(dimethyamino)ethyl methacrylate (DM).

In one embodiment, the repeating unit having latent negatively charged group is derived from 2,2,2-trifluoroethyl methacrylate (TFE), and the positively charged repeating unit is derived from 2-(dimethyamino)ethyl methacrylate (DM).

Representative monomers with latent negatively charged groups, IB or TFE, were mixed with positively charged DM monomer, and AIBN were mixed in ethanol. The solution was purged by argon and sealed in a vial under argon. The solution was continuously stirred and polymerized at 60° C. to yield a copolymer solution. Aluminum or epoxy-coated aluminum coated panels were coated using the dip-in method. Protein adsorption was evaluated by ELISA after the coated sample surface was hydrolyzed in 3.5% NaCl solution (pH 8.3) at 37° C. for different time intervals. The results shown in FIG. 14 demonstrate that with the hydrolysis of the latent negatively charged groups, the protein adsorption on the hydrogel coated surface decreases.

The copolymers and hydrogel of the present invention are substantially electronically neutral when the latent negatively charged groups are converted to negatively charged groups. Therefore, the number of the repeating units having latent negatively charged groups and the number of positively charged repeating units are substantially equal. In one embodiment, the ratio of the number of the repeating units having latent negatively charged groups and the number of the positively charged repeating unit is from about 1:1.1 to about 1:0.5.

The copolymers and the hydrogels of the present invention can further include a plurality of repeating units having a hydrophobic pendant group. The hydrophobic group can be any substituted or unsubstituted alkyl, alkenyl, alkynyl, phenyl, and ester group. In one embodiment, the hydrophobic group is a lauryl methacrylate (C12).

Copolymers and Hydrogels with Negatively Charged Group and Latent Positively Charged Groups In one embodiment, the present invention provides a copolymer, comprising, (a) a plurality of negatively charged repeating units; and (b) a plurality of repeating units having latent positively charged groups reactive to provide positively charged groups, wherein the copolymer is substantially electronically neutral when the latent positively charged groups are converted to positively charged groups.

The copolymer can be crosslinked to provide a hydrogel.

The latent positively charged group is a group that can be converted to a positively charged group upon the exposure to an appropriate environmental stimulus. Representative environmental stimuli include oxidants, reductant, heat, light, acids, bases, enzymes, and electromagnetic field. The latent positively charged groups can be an amide group, an imide group, and an oxyimino group that can be converted to positively charged amine group or imine group upon exposure to proper stimuli. Representative positively charged pendant group is selected from the group consisting of quaternary ammonium groups, primary amine groups, secondary amine groups, tertiary amine groups, quaternary phosphonium groups, tertiary phosphonium groups, amide groups, heteroaromatic nitrogen groups, and sulfonium groups.

The repeating unit having a latent positively charged group can be derived from a monomer having a latent positively charged group. Representative monomers include imide groups and oxyimino groups.

The copolymers and hydrogels of the present invention are substantially electronically neutral when the latent positively charged groups are converted to positively charged groups. Therefore, the number of negatively charged repeating units and the number of the repeating units having latent positively charged groups are substantially equal. In one embodiment, the ratio of the number of the negatively charged repeating units and the number of the repeating unit having latent positively charged group is from about 1:1.2 to about 1:0.8.

Polymer with Latent Negatively Charged Groups and Latent Positively Charged Groups In one embodiment, the present invention provides a copolymer, comprising, (a) a plurality of repeating units having latent negatively charged groups reactive to provide negatively charged groups; and (b) a plurality of repeating units having latent positively charged groups reactive to provide positively charged groups, wherein the copolymer is substantially electronically neutral when the latent negatively charged groups are converted to negatively charged groups, and the latent positively charged groups are converted to positively charged groups.

The copolymer can be crosslinked to provide a hydrogel.

The copolymers and hydrogel of the present invention are substantially electronically neutral when the latent negatively charged groups are converted to negatively charged groups and the latent positively charged groups are converted to positively charged groups. Therefore, the number of repeating units having latent negatively charged groups and the number of the repeating units having latent positively charged groups are substantially equal. In one embodiment, the ratio of the number of the repeating units having latent negatively charged groups and the number of the repeating unit having latent positively charged group is from about 1:1.1 to about 1:0.5.

Figure 7:
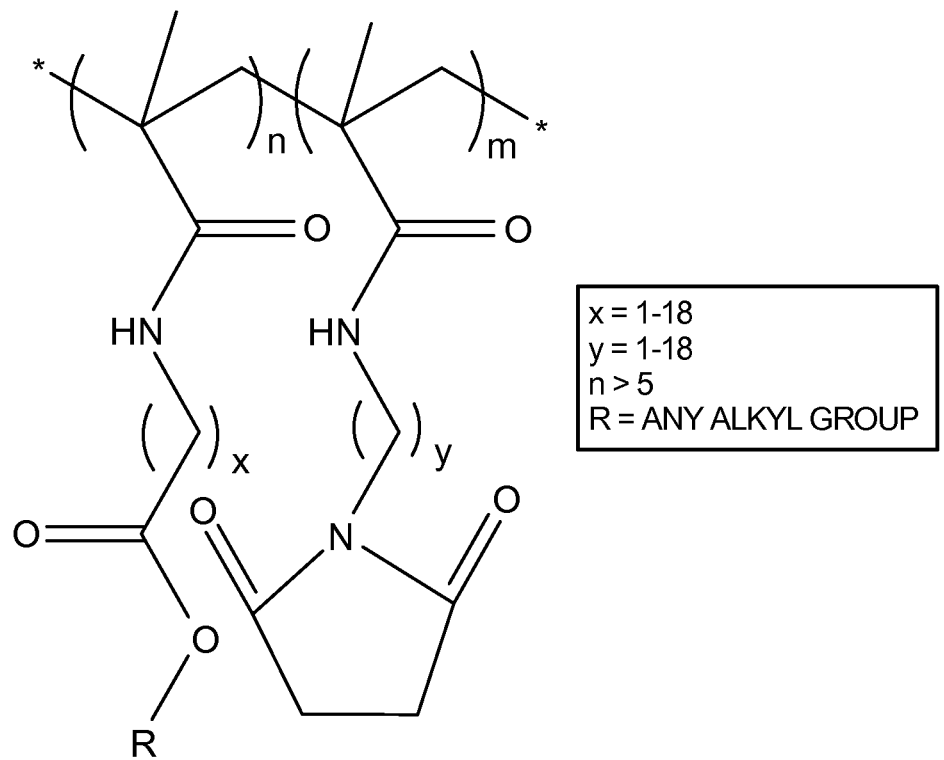
FIG. 7 is a schematic illustration of a representative copolymer with latent negatively charged groups as carboxylate groups and latent positively charged groups as imide groups.

In one embodiment, the copolymers and hydrogels of the present invention have a plurality of repeating units having ester groups as the latent negatively charged groups and a plurality of repeating units having imide groups as the latent positively charged group as shown in FIG. 7. After hydrolysis, the latent negatively charged group, ester group, is converted to corresponding negatively charged carboxylic group, and the latent positively charged group, imide group, is converted to corresponding positively charged amine group.

Figure 9:
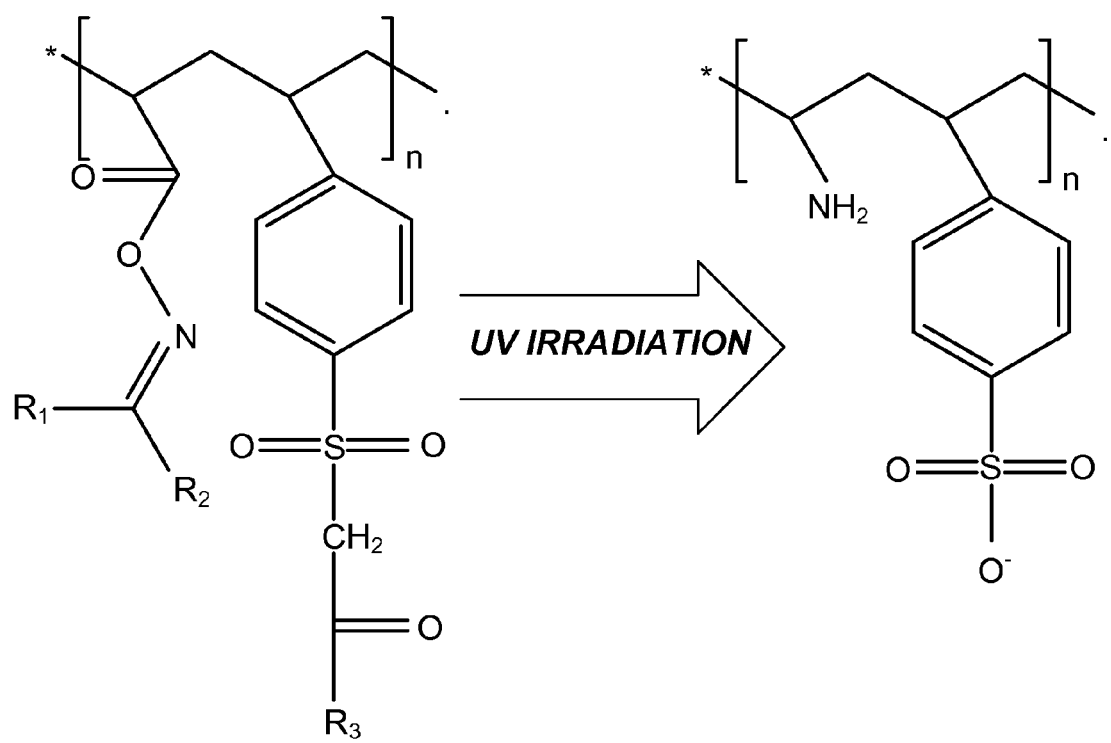
FIG. 9 is a schematic illustration of a representative copolymer with latent negatively charged groups as beta-ketosulfone groups and latent positively charged groups as oxyimino groups.

In one embodiment, the copolymers and hydrogels of the present invention have a plurality of repeating units having beta-ketosulfone groups as the latent negatively charged groups and a plurality of repeating units having oxyimino groups as the latent positively charged groups, as shown in FIG. 9. Upon exposure to UV radiation, the latent negatively charged group, beta-ketosulfone group, is converted to negatively charged sulfuric group, and the latent positively charged group, oxyimino group, is converted to positively charged amine group.

Copolymers and Hydrogels with Additional Others Types Repeating Units

The copolymers and hydrogels of the present invention may further comprise others types of repeating units. For example, the copolymer may further comprise a plurality of repeating units having a hydrophobic pendant group.

In one representative embodiment, the repeating units having a hydrophobic pendant group is laurylate methacrylate (C12).

In one embodiment, C12 derived repeating units are incorporated into mixed charged copolymer DM-SA to afford C12-DM-SA copolymer. In one embodiment, C12 derived repeating units are incorporated into mixed charged copolymer DM-CA to afford C12-DM-CA copolymer.

Mixed charged compounds can be used to prepare nonfouling copolymers containing hydrophobic pendant groups if the charge balance can be well controlled for the copolymers. In preparing the representative mixed charged compounds containing hydrophobic pendant moieties, a mixture of DM, SA, C12, and AIBN were dissolved in a mixture of ethanol and methanol. The solution was purged with nitrogen, and was continuously stirred and polymerized for 24 hours to afford the copolymer. An aluminum or epoxy-coated aluminum chips were coated with dip coating methods. Enzyme-Linked Immunosorbent Assay (ELISA) was used to evaluate the protein adsorption on the copolymers. The composition characterization of mixed charged polymers containing hydrophobic groups is carried out by X-ray photoelectron spectroscopy.

Figure 3:
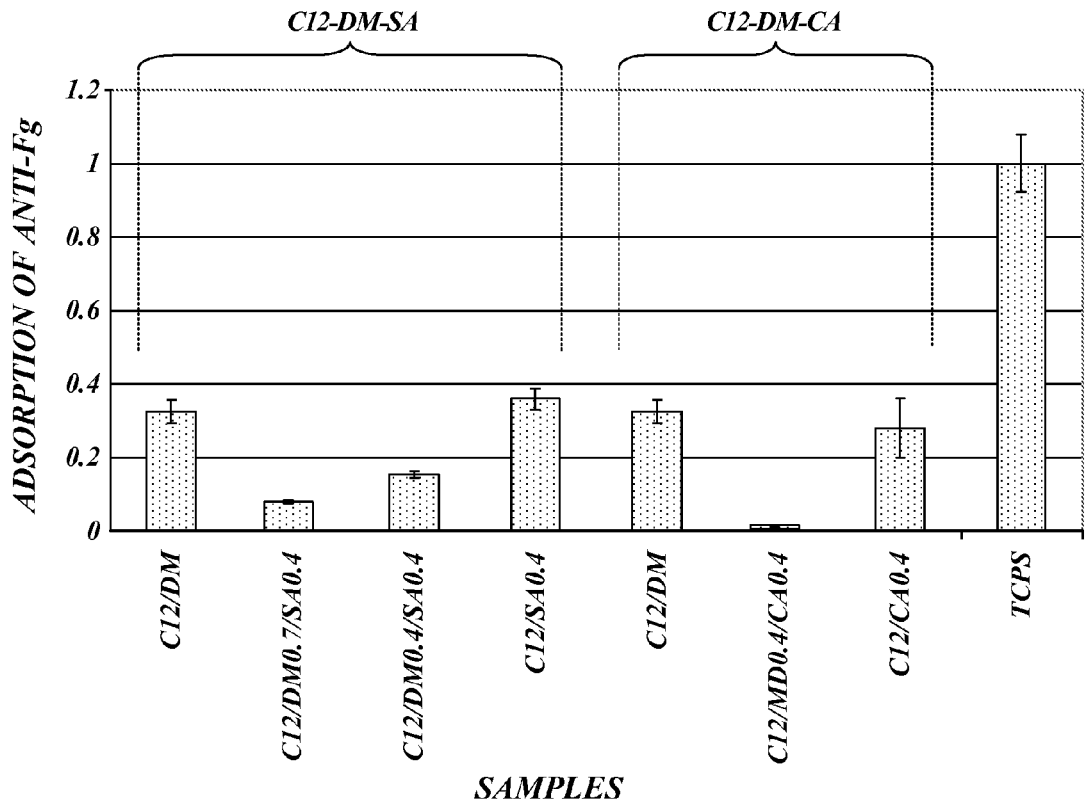
FIG. 3 compares the HRP conjugated anti-fibrinogen adsorption on hydrogels from 150 mM, pH 7.4 PBS. C12/DM0.7/SA0.4 represents molar ratios of C12, DM, and SA of 1:0.7:0.4 in the polymerization solution.
Figure 4:
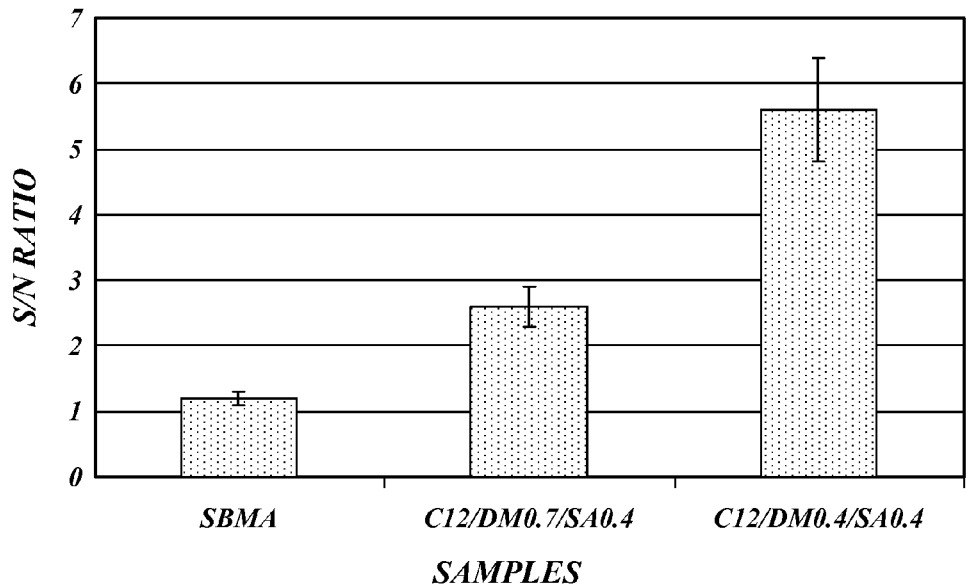
FIG. 4 compares the ratio of sulfur to nitrogen (S/N) in SBMA, $C12/DM_{0.7}/SA_{0.4}$, and $C12/DM_{0.4}/SA_{0.4}$ coatings determined by x-ray photoelectron spectroscopy. The results show about 1:1 S/N ratio for zwitterionic SBMA and preferential polymerization for the SA component in the copolymers.

As shown in FIG. 3, for both C12-DM-SA and C12-DM-CA copolymers, protein adsorption shows a U shaped curve (i.e., lower protein adsorption in the middle range of compositions) as observed previously for mixed charged SAMs. For the C12-DM-SA system, a better result is obtained on C12/$DM_{0.7}$/$SA_{0.4}$ (0.7 or 0.4 represents the molar compositions in the synthesis solution). The x-ray photoelectron spectroscopy (XPS) analysis (FIG. 4) shows that the surfaces prepared from C12/$DM_{0.7}$/$SA_{0.4}$ have a N/S ratio closer to 1:1 than those prepared from C12/$DM_{0.4}$/$SA_{0.4}$, indicating a more balanced charge and resulting in lower protein adsorption. The difference in solution and surface composition is due to preferential kinetics during polymerization. For the C12-DM-CA copolymer, very low protein adsorption was observed on the C12/$DM_{0.4}$/$CA_{0.4}$ copolymer coating, indicating that the charged groups are well mixed in this copolymer.

Not wanting to be limited by the theory, it is believed that the reason that the C12/$DM_{0.4}$/$CA_{0.4}$ copolymer coating achieved even lower protein adsorption than the C12/$DM_{0.7}$/$SA_{0.4}$, as shown in FIG. 3, results from differing distributions of charged groups in each system. Because SA is a salt, it is difficult to dissolve once the copolymer is formed. Thus, the distribution of the charged group may not be homogenous. It is likely that the final C12-DM-SA copolymer is in the form of nanoparticles (or particles) because it was not well dissolved in the methanol/propanol solvent. For the C12-DM-CA copolymer, both DM and CA are compatible. They are less charged, easier to dissolve in the organic solvent used in synthesis, and easier to form a more homogenous copolymer. Thus, the solubility of each compound in the solvent used to form the copolymer and in the products can greatly affect the nonfouling properties of the resulting materials.

In one embodiment, C12 derived repeating units and Me derived repeating units are incorporated into mixed charged copolymer DM-GL to afford C12-Me-DM-GL hydrogel.

C12, GL, Me, and DM in a 1:1:1:1 molar ratio and AIBN were mixed in Ethyl acetate. The solution was purged by nitrogen. The solution was continuously stirred and polymerized at 60° C. under nitrogen to yield a copolymer solution. Aluminum or epoxy-coated aluminum coated panels were coated using the dip-in, brush, or spray method with the copolymer solution. Protein adsorption was evaluated by ELISA after the coated sample surface was hydrolyzed in 3.5% NaCl solution (pH 8.3) at 25° C. for different time intervals. The results in shown FIG. 13 demonstrate that with the hydrolysis of the latent negatively charged groups, the protein adsorption on the hydrogel coated surface decreases.

Copolymers and Hydrogels Derived from Amino Acids

In one embodiment, the nonfouling copolymers and hydrogels of the present invention are peptides formed from amino acids monomers with positively charged side groups, latent positively charged side groups, negatively charged side groups, or latent negatively charged side groups. The latent positively or negatively charged side groups can be converted into positively or negatively charged groups after being exposed to the environment stimuli, such as an oxidant, a reductant, heat, light, an acid, a base, or an enzyme.

The amino acid monomers useful to the present invention can be natural amino acids or synthetic amino acids.

Representative amino acids having negatively charged groups useful in the present invention include amino acids containing a carboxylic group such as aspartic acid, glutamic acid, or amino acids containing an acidic hydroxyl group on an aromatic ring, such as tyrosine.

Representative amino acids having latent negatively charged groups include esters or amides of aspartic acid and glutamic acid, and precursors of sulfate and carboxyl groups such as cysteine, cystine, and serine. For the copolymers and hydrogels that include aspartic acid or glutamic acid derived repeating units, the side chain carboxylic acid groups from aspartic acid or glutamic acid derived units can be further modified. For example, the carboxylic acid groups can be attached to a drug, a cell adhesive group such as RGD, or an antibiotics via a ester or an amide bond.

Representative amino acids having positively charged groups useful in the present invention include the amino acids with amine side groups such as lysine and arginine, the amino acids with nitrogen atom in aromatic rings such as histidine and tryptophan, and the amino acids with nitrogen atom in an amide such as asparagines and glutamine.

Figure 5:
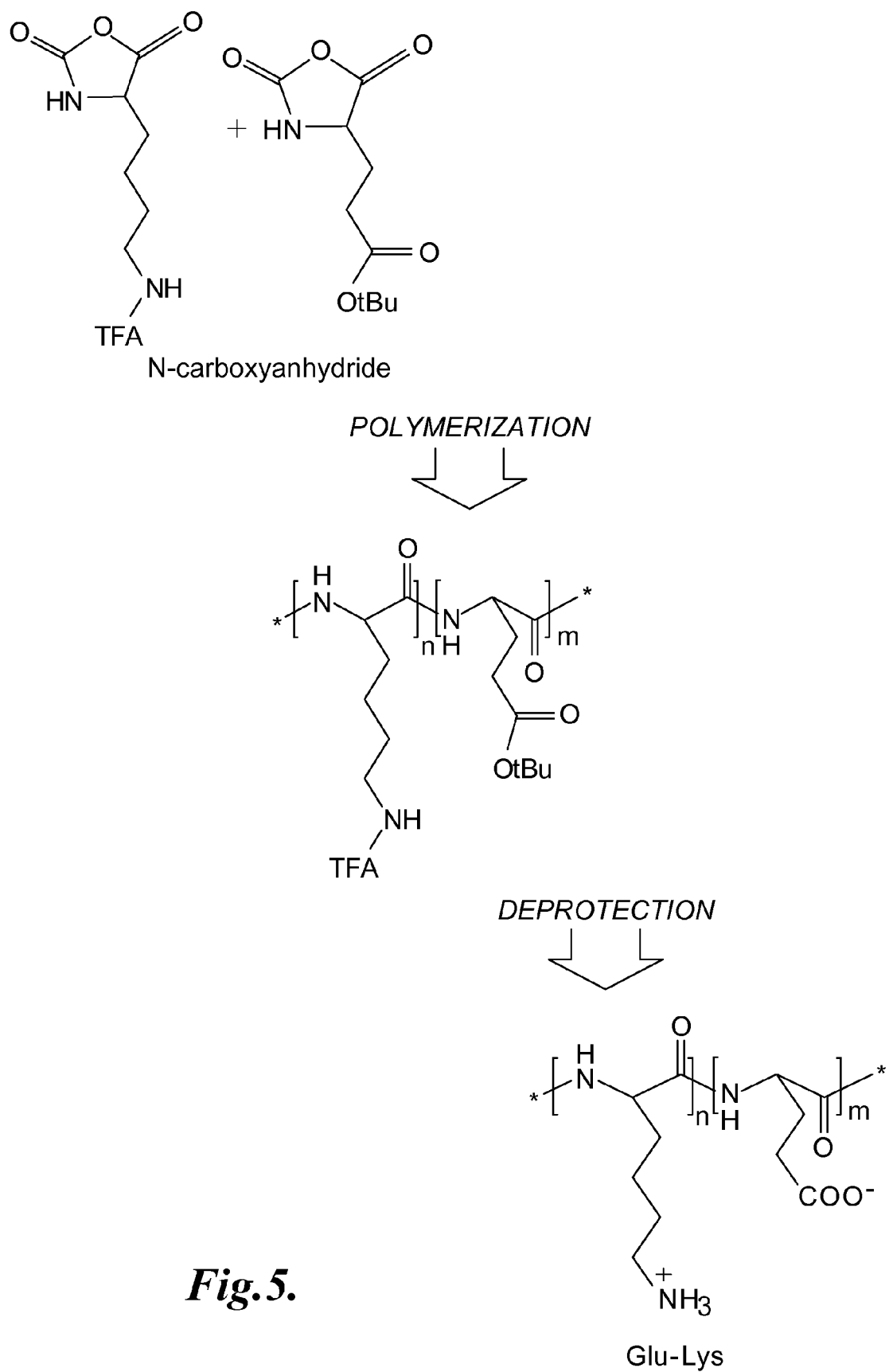
FIG. 5 is a schematic illustration of the synthesis of a representative copolymer with the negatively charged repeating units derived from glutamic acid and the positively charged repeating units derived from lysine.

In one embodiment, as shown in FIG. 5, the repeating units with negatively charged pendant groups are derived from glutamic acid and the repeating units with positively charged pendant groups are derived from lysine. The glutamic acid-derived units and the lysine-derived units are mixed at the nano-scale level therefore the opposite charged groups are distributed uniformly throughout the polymer.

Figure 11:
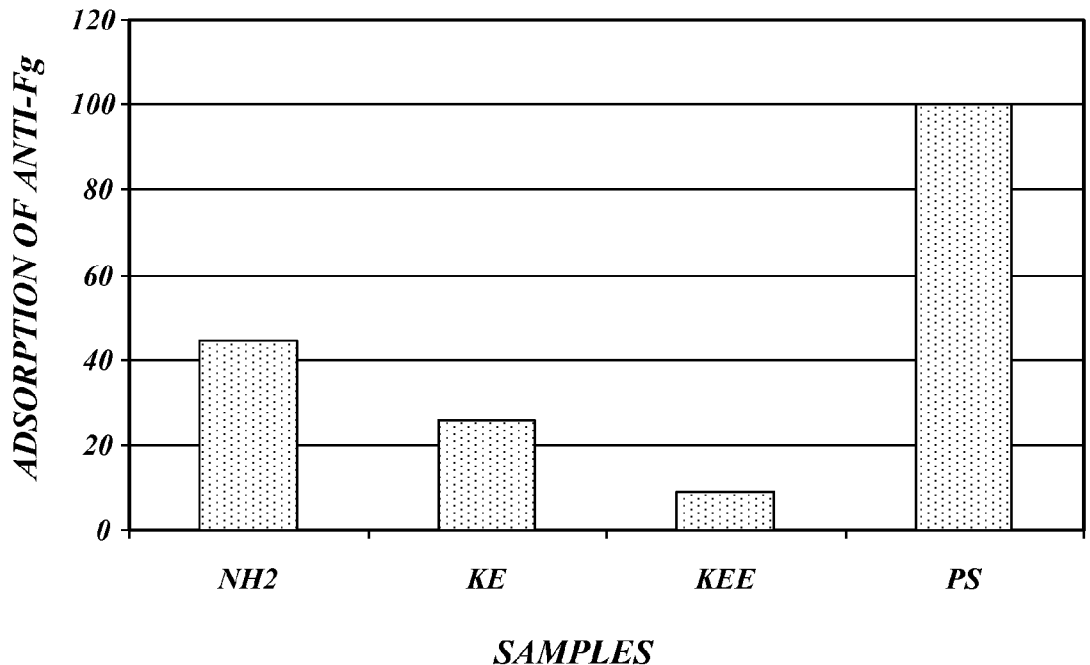
FIG. 11 compares the relative IgG adsorption on the beads coated with representative amino acid-based copolymers. The data was normalized to anti-fibronogen on polystyrene (PS) as 100% ML.

Representative nonfouling peptides were synthesized on the TentaGel S NH2 resin using standard Fmoc chemistry. The coupling reaction was carried out after the Fmoc deprotection with 200 mL/L piperidine in DMF. The side chains of the peptides were deprotected. Results from enzyme-linked immunosorbent assay (ELISA) experiments graphed in FIG. 11 show that neutral KEE (KEKEKEE) has higher resistance to Fg and IgG than slightly positive TentaGel S NH2 resin, KE (KEKEKEKE), and polystyrene beads.

The peptides of the present invention can be crosslinked with a crosslinker molecule having two reactive groups, such as a diacid. Representative amino acid-based crosslinkers include dimethyl L-cystine and N,N'-didansyl-L-cystine. These crosslinkers can be mixed with amino acid-based copolymers and cast onto surfaces to form films.

The peptides of the present invention can be linked with other moieties. For example, some of the pendant groups can be used to link to other moieties through ester or amide bonds. The other moieties can be hydrophobic groups, hydrophilic groups, moieties derived from drugs, cell adhesive moieties, or moieties derived from antibiotics.

In one embodiment, the amino acid-based copolymers and hydrogels of the present invention can further include a plurality of repeating units having a hydrophobic pendant group.

The amino acid-based copolymers and hydrogels of the present invention are biocompatible, have the minimum immune response, and possess nonfouling properties. These copolymers and hydrogels have varieties of applications.

In one embodiment, the amino acid-based nonfouling copolymers and hydrogels of the present invention can be used as artificial skin. The materials can be used to cover wound sites and protect the wound sites from infection. The mechanical properties of the materials can be adjusted via cross-linking, such as by using cysteine as the crosslinking agent. The materials have high oxygen permeability and can be biodegradable.

Figure 6:
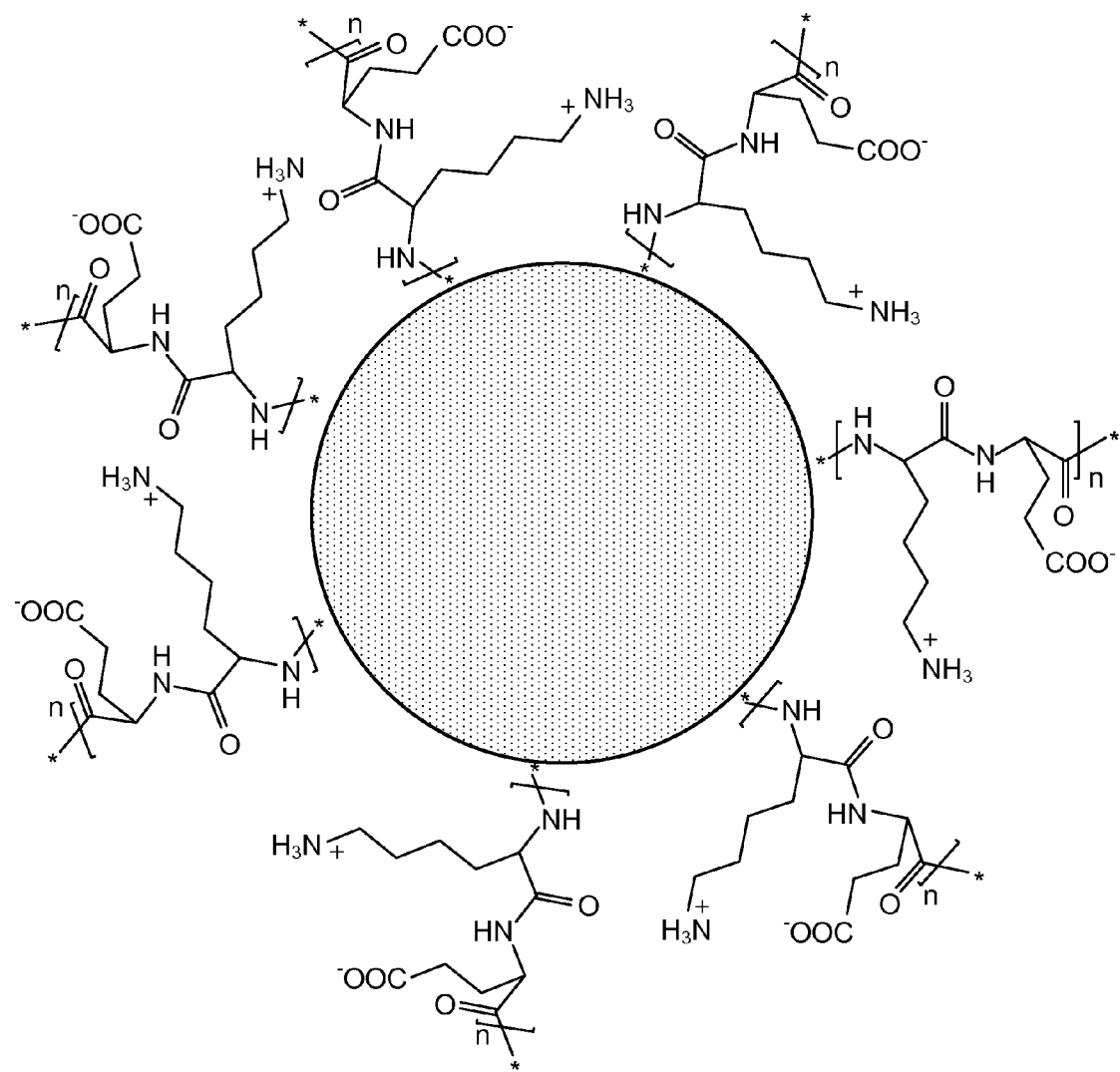
FIG. 6 is a schematic illustration of a functional protein coated with a representative nonfouling copolymer of the present invention.

In one embodiment, the amino acid-based nonfouling copolymers and hydrogels can be used to coat nucleic acids, proteins or peptides, or small molecular drugs or diagnostic agents. For example, as shown in FIG. 6, the amino acids-based nonfouling copolymers and hydrogels can be conjugated with a functional protein. Because the nonfouling coatings can reduce the interactions between enzymes and functional proteins, the modification will slow down the functional proteins' enzymatic degradation and elongate the circulation time.

Because the amino acids-based nonfouling materials have excellent stability in blood and prolonged life time in blood, these material are well suited for systemic delivery. For example, these amino acids-based nonfouling materials can be used for gene and drug delivery. When used for gene delivery, the ratio of positive to negative amino acid groups can be adjusted so that the material can not only condense nuclei acids, but also maintain their nonfouling behavior.

In one embodiment, the nonfouling copolymers and hydrogels can be used as coatings of implants such as stents, catheters, and vascular grafts. In one embodiment, the nonfouling copolymers and hydrogels can be used for coatings for medical devices.

The amino acids-based nonfouling materials provided in the present invention can be made by using genetic engineering methods or chemical synthesis. In one embodiment, the amino acids-based nonfouling material is made by using *E. coli*, yeast, or other in vitro expression system. In one embodiment, the amino acids-based nonfouling material is made by sequential preparation methods, i.e., combining amino acids one by one in a sequential order. For example, the synthesis can be carried out by using a peptide synthesizer. In one embodiment, the amino acids-based nonfouling material is synthesized by polymerizing the amino acid-based monomers, such as N-carboxyanhydrides as shown in FIG. 5, to afford copolymers with uniform distribution of the opposite charged groups.

Copolymers Grafted onto a Surface Via Atom Transfer Radical Polymerization (ATRP)

In one embodiment, the copolymers of the present invention can be synthesized directly on a substrate surface. The mixed charged copolymers can be grafted onto a surface via atom transfer radical polymerization (ATRP) from monomers having oppositely charged groups. The copolymers grafted on the surface can form substantially electronically neutral polymer brushes having nonfouling properties.

In one embodiment, the negatively charged repeating unit is derived from 2-carboxyethyl acrylate (CA), and the positively charged repeating unit is derived from 2-(dimethylamino)ethyl methacrylate (DM).

In one embodiment, the negatively charged repeating unit is derived from 2-carboxyethyl acrylate (CA), and the positively charged repeating unit is derived from 2-(diethylamino)ethyl methacrylate (DE).

In one embodiment, the negatively charged repeating unit is derived from 2-carboxyethyl acrylate (CA), and the positively charged repeating unit is derived from [2-(methacryloyloxy)ethyl]trimethylammonimium chloride (TM).

In one embodiment, the negatively charged repeating unit is derived from 2-carboxyethyl acrylate (CA), and the positively charged repeating unit is derived from 2-aminoethyl methacrylate hydrochloride (NH2).

In one embodiment, the negatively charged repeating unit is derived from 3-sulfopropyl methacrylate potassium salt (SP), and the positively charged repeating unit is derived from 2-(dimethylamino)ethyl methacrylate (DM).

In one embodiment, the negatively charged repeating unit is derived from 3-sulfopropyl methacrylate potassium salt (SP), and the positively charged repeating unit is derived from 2-(diethylamino)ethyl methacrylate (DE).

In one embodiment, the negatively charged repeating unit is derived from 3-sulfopropyl methacrylate potassium salt (SP), and the positively charged repeating unit is derived from 2-aminoethyl methacrylate hydrochloride (NH2).

In one embodiment, the positively charged repeating unit of the copolymer grafted on a surface via ATRP is derived from a quaternary amine monomer, [2-(methacryloyloxy)ethyl]trimethyl ammonium chloride (TM), and the negative charged repeating unit is derived from a sulfonic acid monomer, 3-sulfopropyl methacrylate potassium salt (SP).

The nonfouling property of a representative copolymer grafted on a surface via ATRP was compared with a positive polymer and a negative polymer. The copolymer was synthesized from a reaction mixture composed of a 2:1 molar ratio of a quaternary amine monomer, [2-(methacryloyloxy)ethyl] trimethyl ammonium chloride, to a sulfonic acid monomer, 3-sulfopropyl methacrylate potassium salt. The positive polymer was synthesized from a reaction mixture of [2-(methacryloyloxy)ethyl] trimethyl ammonium chloride. The negative polymer was synthesized from a reaction mixture of 3-sulfopropyl methacrylate potassium salt.

A bromine terminated thiol molecule was used to initiate the ATRP reaction in the presence of copper (I) bromide and 2,2'-dipyridyl (BPY). The monomers were dissolved in 10 mL of a 1:1 volume mixture of methanol and water, and the BPY was dissolved in 10 mL of methanol. The thiol self-assembled monolayers (SAMs) were formed overnight in a 0.1 mM solution in ethanol. Protein adsorption was tested on surface plasmon resonance (SPR) biosensors. The adsorption from 1 mg/mL solutions of bovine serum albumin (BSA), lysozyme (LYZ), and fibrinogen (FG) were tested on separate channels.

Figure 10:
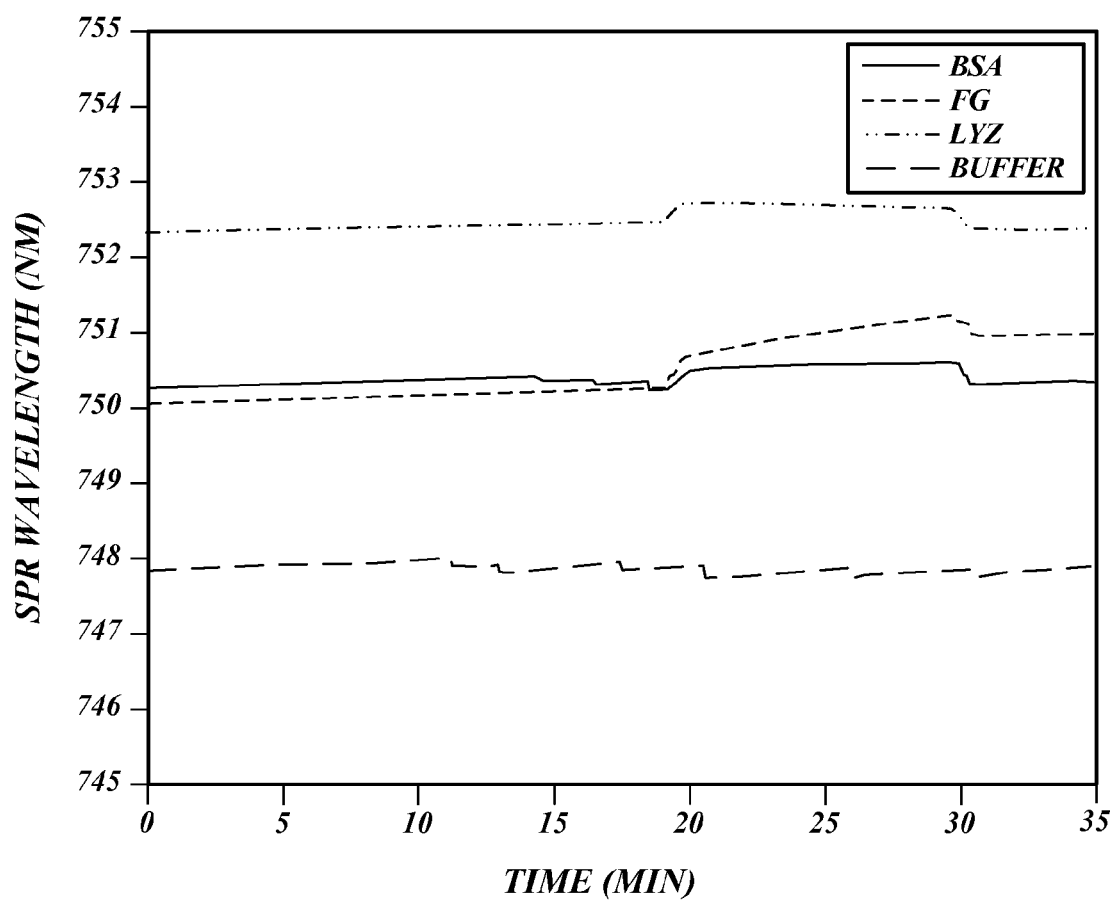
FIG. 10 compares the SPR spectrograms of protein adsorption showing the binding of 1 mg/mL protein solutions of bovine serum albumin (BSA), lysozyme (LYZ), and fibronogen (FG) on representative mixed charged polymers grafted on a substrate surface via ATRP.

FIG. 10 shows representative SPR spectrograms of protein adsorption on the mixed charged polymers grafted via ATRP. It can be seen that the surface with the mixed charged copolymers has low protein adsorption when compared to either of the individually charged monomers (Table 1). The total SPR wavelength shift corresponding to the binding of the three proteins on each of the surfaces is summarized in Table 1. This data is based on SPR data obtained from 2 separate SPR chips formed at the same time (same ATRP reaction). From Table 1, it can be seen that there is significant FG and BSA binding to the positively charged surface, while there is minimal LYZ binding. The opposite trend was seen on the negatively charged surface where is can be seen that there is significant LYZ binding, along with noticeable FG binding and some limited BSA binding.

TABLE 1

Summary of protein adsorption on mixed charged polymers grafted via ATRP (in nm of wavelength shift and 1 nm wavelength shift in SPR is equivalent to 0.15 mg/m$^2$ adsorbed proteins)

| | Positive Polymer | Negative Polymer | 2:1 Mixture |
|---|---|---|---|
| BSA | 14.9 | 1.0 | 0.4 |
| FG | 38.7 | 7.1 | 0 |
| LYZ | 0 | 13.3 | 0 |

EXAMPLES

Materials and Methods. 2-(Dimethylamino)ethyl methacrylate (DM), 2-(diethylamino) ethyl methacrylate (DE), [2-(methacryloyloxy)ethyl] trimethylammonium chloride (TM), 2-carboxyethyl acrylate (CA), acrylic acid (AA), 3-sulfopropyl methacrylate potassium salt (SA), lauryl methacrylate (C12), oligo(ethylene glycol) methacrylate (OEG, typical Mn=300), 2-hydroxyethyl methacrylate (HEMA) were purchased from Sigma-Aldrich and used as received. Aminoethyl methacrylate hydrochloride (NH2) and triethylene glycol dimethacrylate (TEGDMA) were purchased from polyscience, Inc. (Warrington, Pa.).

Protein Adsorption Evaluated by Enzyme-Linked Immunosorbent Assay (ELISA). To measure Fg adsorption, all of the samples were first incubated with 1 mg/ml Fg for 1.5 hours, followed by 5 washes with PBS buffer. Samples were then incubated with horseradish peroxidase (HRP) conjugated anti-fibrinogen (~10 μg/ml) for 1.5 hours in a buffer under a desirable conditions, followed by another 5 washes with the same buffer. The sample in 1 mg/ml o-Phenylenediamine (OPD) 0.1 M citrate-phosphate pH 5.0 buffer containing 0.03% hydrogen peroxide was added. Enzyme activity was stopped by adding an equal volume of 2N $H_2SO_4$ after 30 minutes. The tangerine color is measured at 492 nm. To measure anti-Fg adsorption, samples are directly incubated with 10 μg/ml horseradish peroxidase (HRP) conjugated anti-Fg, following the same steps for the measurements of Fg adsorption.

Example 1

Preparation of Representative Mixed Charged Hydrogels

Preparation of Mixed Charged Hydrogels: 1 mmole of positively charged and 1 mmole negatively charged monomers in a 0.5 ml mixed solvent of ethylene glycol/ethanol/$H_2O$ (1.5:1:1.5) were mixed with 20 μl TEGDMA, 8 μl 40% ammonium persulfate (APS) and 8 μl 15% sodium metabisulfite (SMS). The mixture was put between two glass slides with 0.38 mm space, sealed with parafilm, put into a 60° C. oven for one hour, and left at room temperature for 3 hours. For gel preparation, some compounds can be kinetically preferred over others when they are copolymerized at room temperature with APS and SMS as initiators and the final composition of each component in the hydrogel can slightly deviate from the 1:1 ratio as in the solution, leading to unbalanced charge for mixed charged hydrogels and protein adsorption. This issue can be largely resolved by raising the reaction temperature to 60° C. The hydrogel was taken out and soaked in 0.15M pH 7.4 PBS overnight and punched into small disks of 5 mm, and soaked in fresh 0.15M PBS overnight again before enzyme-linked immunosorbent assay (ELISA) experiments.

Protein Adsorption Evaluated by Enzyme-Linked Immunosorbent Assay (ELISA): To measure Fg adsorption, all of the samples including the hydrogel disks, dip coated chips and tissue culture polystyrene (TCPS) substrates, were first incubated with 1 mg/ml Fg for 1.5 hours, followed by 5 washes with PBS buffer. Samples were then incubated with horseradish peroxidase (HRP) conjugated anti-fibrinogen (~10 µg/ml) for 1.5 hours in a buffer under a desirable conditions, followed by another 5 washes with the same buffer. The hydrogel disks, dip coated panels and TCPS substrates were taken out and put into 24 wells plates. 800 µl mg/ml o-phenylenediamine (OPD) 0.1 M citrate-phosphate pH 5.0 buffer, containing 0.03% hydrogen peroxide was added. Enzyme activity was stopped by adding an equal volume of 2N $H_2SO_4$ after 15 minutes. The tangerine color is measured at 492 nm. To measure anti-Fg adsorption, samples are directly incubated with horseradish peroxidase (HRP) conjugated anti-Fg, following the same steps for the measurements of Fg adsorption.

Example 2

Preparation of Representative Mixed Charged Copolymers Containing Hydrophobic Groups Preparation of Mixed Charged Copolymers Containing Hydrophobic Groups: 3.5 mmole DM, 2 mmole SA, 5 mmole C12, and 75 mg AIBN were mixed in 22 ml ethanol and 5 ml methanol. The solution was purged with $N_2$ for 30 min. The solution was continuously stirred and polymerized at 60° C. for 24 hours under $N_2$. The solution was cooled down to room temperature after polymerization. A sticky copolymer was formed at the bottom of the flask and dissolved in the xylene. 9 mm×9 mm Al or epoxy-coated Al chips were coated with dip coating methods. For the C12-DM-CA copolymer, the product in solution, which is low degree of polymerization and contains more polar components, prevents protein adsorption.

Figure 13:
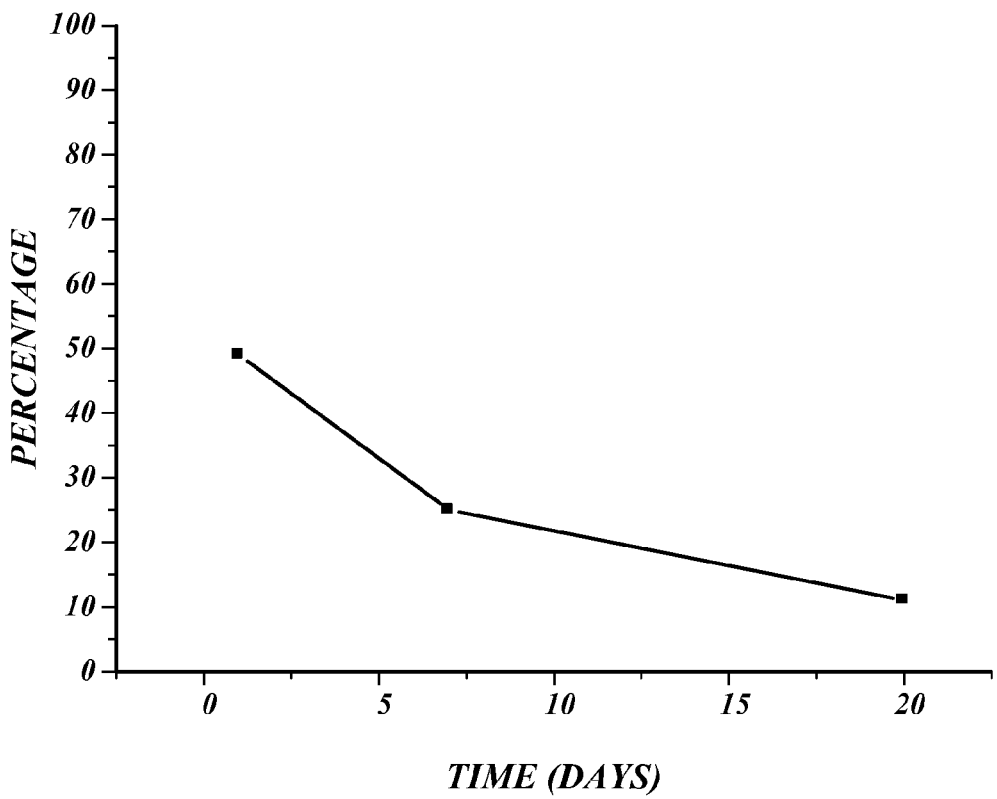
FIG. 13 compares relative anti-fibrinogen adsorption on a representative hydrogel, C12/GL/DM/Me(1:1:1:1), with respect to TCPS from ELISA after the coated sample was hydrolyzed over different time intervals at 25° C.

1.45 ml C12, 1.25 ml GL, 0.53 ml Me, 0.85 ml DM (1:1:1:1 molar ratio) and 100 mg AIBN were mixed in 25 ml Ethyl acetate. The solution was purged by $N_2$ for 30 minutes. The solution was continuously stirred and polymerized at 60° C. for 24 hours under $N_2$ stream. The solution was cooled down to room temperature after polymerization. Most solvents were evaporated to yield 10 ml sticky copolymer solution. Al or epoxy-coated Al coated panels were coated using the dip-in, brush, or spray method with the copolymer solution. Protein adsorption was evaluated by ELISA after the coated sample surface was hydrolyzed in 3.5% NaCl solution (pH 8.3) at 25° C. for different time intervals as shown in FIG. 13.

Figure 14:
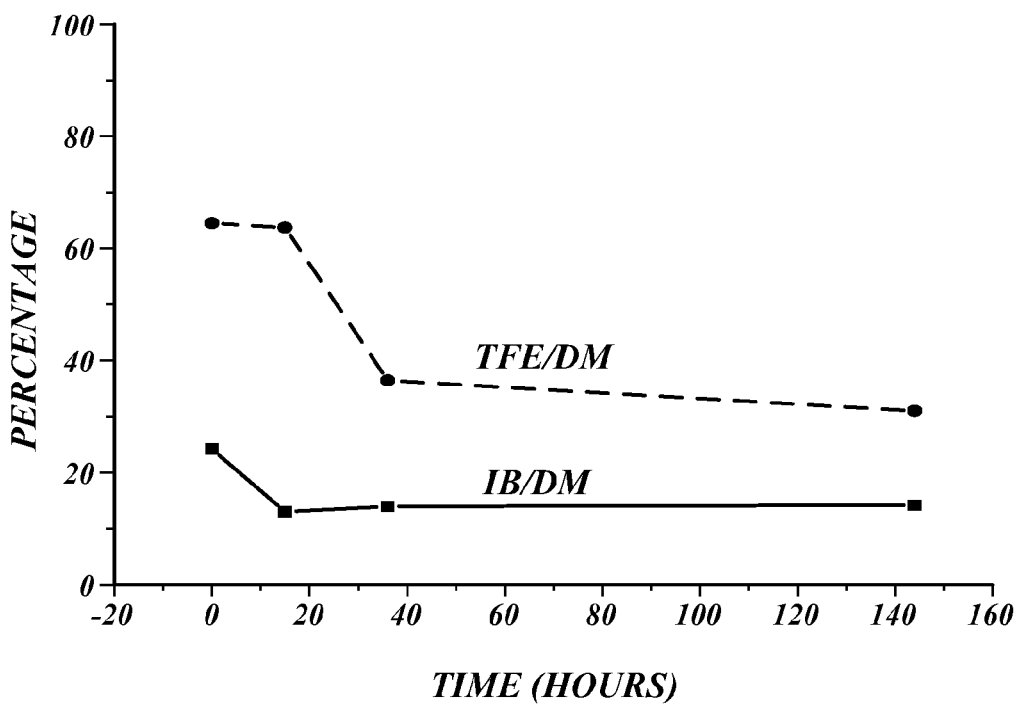
FIG. 14 compares relative anti-fibrinogen adsorption on two representative hydrogels, IB/DM and TFE/DM, with respect to TCPS from ELISA after the coated sample was hydrolyzed over different time intervals at 37° C. The data was normalized to anti-fibrinogen on TCPS as 100% ML).

163 µl IB or 142.3 µl TFE, 170 µl DM, and 15 mg AIBN were mixed in 5.4 ml ethanol. The solution was purged by Ar for 3 min. and sealed in a 7 ml vial under Ar. The solution was continuously stirred and polymerized at 60° C. for 48 hours. The solution was cooled down to room temperature after polymerization. Most solvents were evaporated to yield 1.5 ml sticky copolymer solution. Al or epoxy-coated Al coated panels were coated using the dip-in method. Protein adsorption was evaluated by ELISA after the coated sample surface was hydrolyzed in 3.5% NaCl solution (pH 8.3) at 37° C. for different time intervals as shown in FIG. 14.

Composition Characterization of Mixed Charged Polymers Containing Hydrophobic Groups by x-ray photoelectron spectroscopy: Dip coated chips analyzed by XPS were dried thoroughly for over three days. XPS measurements were conducted using a Surface Science Instrument X-Probe spectrometer (Mountain View, Calif.) equipped with a monochromatic Al Kα source (KE=1486.6 eV), a Hemispherical analyzer, and a multichannel detector. All XPS data were acquired at a nominal photoelectron takeoff angle of 55°. SSI data analysis software was used to calculate elemental compositions from peak areas.

Example 3

Preparation of Representative Copolymers and Hydrogels Derived from Amino Acids

Nonfouling peptides were synthesized on the TentaGel S NH2 resin (0.3 g, 150-200 Mm, and 0.45 mmol/g substitution) using standard Fmoc chemistry. The coupling reaction was carried out for 1 h after the Fmoc deprotection with 200 mL/L piperidine in DMF for 10 min. The side chains of the peptides were deprotected for 4 h (100 mg resin/mL) with FA/Phenol/Water/Thioanisole/EDT 82.5/5/5/2.5, followed by one washing with DI water, five washings with DMF, and five washings with DI water. Results from enzyme-linked immunosorbent assay (ELISA) experiments in FIG. 11 show that neutral KEE (KEKEKEE) has higher resistance to Fg (12.8% ML) and IgG (8.7% ML) than slightly positive Tenta-Gel S NH2 resin (treated with TFA/Phenol/Water/Thioanisole/EDT 82.5/5/5/2.5 for 4 hours), KE (KEKEKEKE), and polystyrene beads (PS, 70-90 mesh).

Example 4

Figure 12:
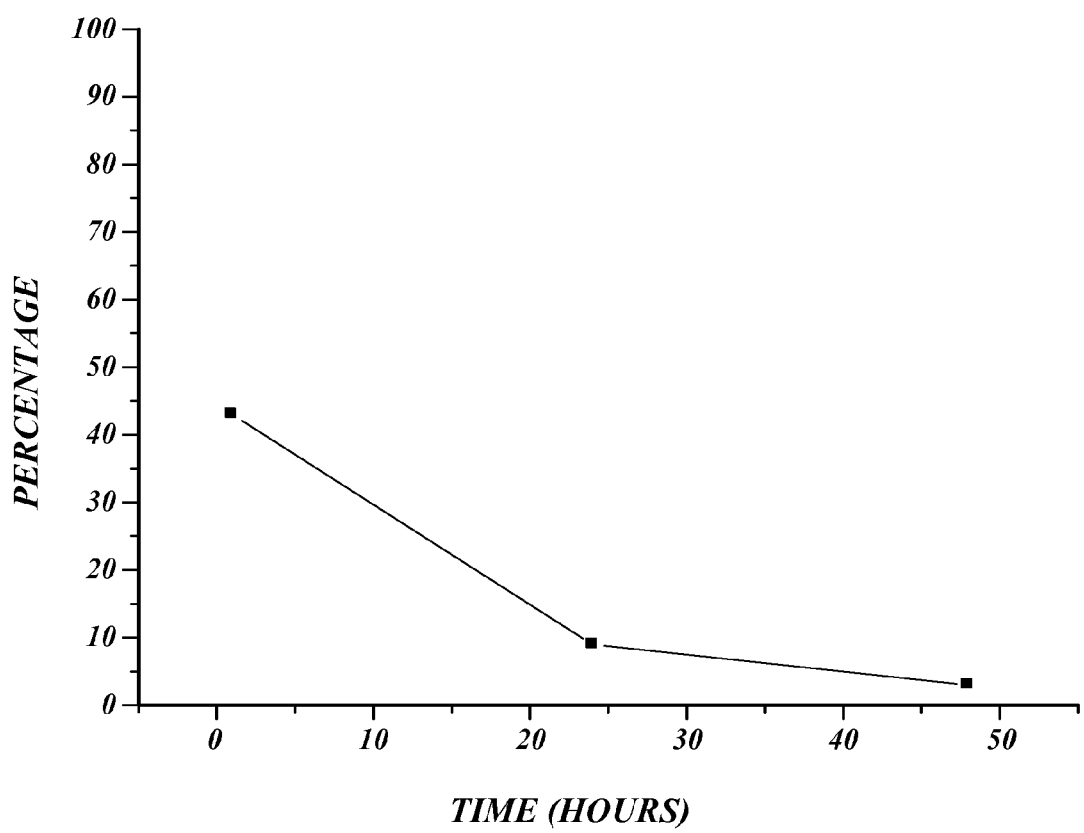
FIG. 12 compares the relative anti-Fibronogen adsorption on a representative hydrogel GL/DM(1:1), with respect to TCPS from ELISA after the coated sample was hydrolyzed over different time intervals at 25° C.

Preparation of Representative Hydrogels with Latent Negatively Charged Groups and Positively Charged Groups 1.25 ml GL and 0.85 ml DM (1:1 molar ratio) along with 50 mg AIBN were mixed in 12 ml Ethyl acetate. The solution was purged by $N_2$ for 30 minutes. The solution was continuously stirred and polymerized at 60° C. for 24 hours under $N_2$ stream. The solution was cooled down to room temperature after polymerization. Most solvents were evaporated to yield 5 ml sticky copolymer solution. Al or epoxy-coated Al coated panels were coated using the dip-in method with the copolymer solution. Protein adsorption was evaluated by ELISA after the coated sample surface was hydrolyzed in 3.5% NaCl solution (pH 8.3) at 25° C. for different time intervals as shown in FIG. 12.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for grafting a copolymer to a surface to provide a substantially electronically neutral polymer brush, comprising:
   (a) immobilizing a bromine terminated alkyl thiol to a surface to provide a monolayer having a plurality of bromine terminated groups;
   (b) contacting the monolayer having a plurality of bromine terminated groups with a polymerization catalyst and a combination of first and second monomers to provide a monolayer of copolymers,
   wherein the first monomer is selected from the group consisting of negatively charged monomers and monomers having latent negatively charged groups reactive to provide negatively charged groups,
   wherein the second monomer is selected from the group consisting of positively charged monomers and monomers having latent positively charged groups reactive to provide positively charged groups, wherein the first and second monomers are present in the combination in substantially equal molar amounts, and wherein each copolymer comprises a plurality of repeating units selected from the group consisting of negatively charged repeating units and repeating units having latent negatively charged groups reactive to provide negatively charged groups, and a substantially equal number of repeating units selected from the group consisting of positively charged repeating units and repeating units having latent positively charged groups reactive to provide positively charged groups;

(c) converting the copolymers having repeating units having latent negatively charged groups to copolymers having repeating units having negatively charged groups, when the first monomers comprise monomers having latent negatively charged groups; and (d) converting the copolymers having repeating units having latent positively charged groups to copolymers having repeating units having positively charged groups, when the second monomers comprise monomers having latent positively charged groups.

2. A substrate comprising a surface having a layer of copolymers grafted therefrom, wherein the layer of copolymers comprises copolymers having:

(a) a plurality of repeating units independently selected from negatively charged repeating units and repeating units having latent negatively charged groups reactive to provide negatively charged groups; and (b) a plurality of repeating units independently selected from positively charged repeating units and repeating units having latent positively charged groups reactive to provide positively charged groups, wherein the copolymer is substantially electronically neutral when the repeating units having latent negatively charged groups and/or repeating units having latent positively charged groups, when present in the copolymer, are hydrolyzed.

3. The substrate of claim 2, wherein the surface is the surface of an implant.

4. The substrate of claim 2, wherein the surface is the surface of a stent, a catheter, or a vascular graft.

5. The substrate of claim 2, wherein the surface is the surface of a medical device.

6. The substrate of claim 2, wherein the surface is the surface of a protein.

7. The substrate of claim 2, wherein one or more of the repeating units are derived from amino acid monomers.

8. The substrate of claim 2, wherein the copolymers are crosslinked.

9. The substrate of claim 2, wherein the surface is a marine surface.

10. The substrate of claim 2, wherein the surface is the surface of a nanoparticle.

11. The substrate of claim 2, wherein the surface is the surface of a biosensor.

* * * * *